United States Patent [19]

Chang

[11] Patent Number: 4,956,171

[45] Date of Patent: Sep. 11, 1990

[54] TRANSDERMAL DRUG DELIVERY USING A DUAL PERMEATION ENHANCER AND METHOD OF PERFORMING THE SAME

[75] Inventor: Yunik Chang, Toms River, N.J.

[73] Assignee: Paco Pharmaceutical Services, Inc., Lakewood, N.J.

[21] Appl. No.: 384,342

[22] Filed: Jul. 21, 1989

[51] Int. Cl.$^5$ .............................................. A61K 9/24
[52] U.S. Cl. ................................. 424/449; 424/448; 514/946
[58] Field of Search .............................. 424/448, 449

[56] References Cited

U.S. PATENT DOCUMENTS

| | | | |
|---|---|---|---|
| 159,852 | 10/1885 | Salpekar | 85/44 |
| 1,390,032 | 4/1921 | Barlow et al. | |
| 2,588,188 | 3/1952 | Cassiere et al. | |
| 3,428,043 | 2/1969 | Shepherd | 128/268 |
| 3,472,931 | 10/1969 | Stoughton | 424/180 |
| 3,598,122 | 8/1971 | Zaffaroni | 128/268 |
| 3,598,123 | 8/1971 | Zaffaroni | 128/268 |
| 3,896,238 | 7/1975 | Smith | 424/358 |
| 3,948,262 | 4/1976 | Zaffaroni | 128/260 |
| 3,952,099 | 4/1976 | Smith | 424/227 |
| 4,264,573 | 4/1981 | Powell et al. | 424/19 |
| 4,286,592 | 9/1981 | Chandrasekaran | 128/260 |
| 4,308,251 | 12/1981 | Dunn et al. | 424/19 |
| 4,310,509 | 1/1982 | Berglund et al. | 424/28 |
| 4,314,557 | 2/1982 | Chandrasekaran | 128/260 |
| 4,379,454 | 4/1983 | Campbell et al. | 604/897 |
| 4,421,737 | 12/1983 | Ito et al. | 424/28 |
| 4,465,660 | 8/1984 | David et al. | 424/15 |
| 4,568,343 | 2/1986 | Leeper et al. | 604/896 |
| 4,573,995 | 3/1986 | Chen et al. | 604/896 |
| 4,588,580 | 5/1986 | Gale et al. | 424/21 |
| 4,593,048 | 6/1986 | Sato et al. | 514/789 |
| 4,605,670 | 8/1986 | Saito et al. | 424/449 |
| 4,615,699 | 10/1986 | Gale et al. | 604/897 |
| 4,626,539 | 12/1986 | Aungst et al. | 514/282 |
| 4,661,521 | 4/1987 | Salpekar | 514/613 |
| 4,699,777 | 10/1987 | Zupon et al. | 424/28 |
| 4,710,497 | 12/1987 | Heller | 514/221 |
| 4,746,515 | 5/1988 | Cheng et al. | 424/449 |
| 4,753,801 | 7/1988 | Oren et al. | 424/465 |
| 4,764,379 | 8/1988 | Sanders et al. | 424/449 |
| 4,865,848 | 9/1989 | Cheng et al. | 424/449 |

OTHER PUBLICATIONS

Z. T. Chowhan and L. Palagyi, "Hardness Increase Induced by Partial Moisture Loss in Compressed Tablets and its Effect on In Vitro Dissolution", in the Journal of Pharmaceutical Sciences, vol. 60, No. 10, Oct. 1978, pp. 1385–1389.

Primary Examiner—Thurman K. Page
Assistant Examiner—Leon R. Horne
Attorney, Agent, or Firm—Seidel, Gonda, Lavorgna & Monaco

[57] ABSTRACT

A transdermal drug delivery system with a dual permeation enhancer is described. The transdermal system comprises a body that contains supplies of drug and a dual permeation enhancer comprising sucrose cocoate and methyl laurate, and has a basal surface that contacts an area of skin and transmits the drug and the dual permeation enhancer to the area for absorption thereby. A method for coadministering a drug and a dual permeation enhancer comprising sucrose cocoate and methyl laurate is also described.

13 Claims, 1 Drawing Sheet

TRANSDERMAL DRUG DELIVERY USING A DUAL PERMEATION ENHANCER AND METHOD OF PERFORMING THE SAME

FIELD OF THE INVENTION

The invention relates to drug delivery systems More particularly, the invention relates to transdermal drug delivery systems utilizing a dual permeation enhancer comprising sucrose cocoate and methyl laurate.

BACKGROUND OF THE INVENTION

Transdermal delivery of drugs provides many advantages over other administrative routes. A number of different transdermal delivery systems have been proposed for administering a wide variety of drugs or other active agents. For example, U.S. Pat. Nos. 3,598,122; 3,598,123; 4,379,454; 4,286,592; 4,314,557 and 4,568,343 all disclose basic transdermal systems.

Despite the development of the transdermal art, there has remained a continuing need for improved techniques and compositions for effective drug delivery. Often, the rate at which a particular drug or beneficial agent is absorbed by the skin is well below the rate necessary to provide a therapeutically beneficial effect. This is especially true of potent opioids, like hydromorphone and buprenorphine, which are useful as analgesics in the treatment of moderate and severe pain.

The analgesic activities of hydromorphone and buprenorphine are about 7 and 30 times more potent than morphine, respectively. Hydromorphone is currently available in various forms such as tablets, syrup, injectables and suppositories under the trade name, Dilaudid ® through Knoll Pharmaceutical Corporation. Buprenorphine is currently available in an injectable hydrochloride form as a parenteral solution under the trade name, Buprenex ® through Norwich Eaton Pharmaceutical Corporation. None of these forms currently provide for effective transdermal delivery of either hydromorphone or buprenorphine.

U.S. Pat. No. 4,626,539 discloses a method of administering an opioid to the systemic circulation of a mammal. The formulation disclosed consists of an effective amount of an opioid, a penetration enhancer, and a carrier vehicle. The enhancer includes at least one of a saturated fatty acid of 8–15 carbon atoms or of an unsaturated fatty acid of 8–18 carbon atoms. The carrier vehicle preferably includes propylene glycol which makes up 30–80% of the total formulation.

U.S. Pat. No. 4,615,699, discloses a reservoir-type transdermal delivery system for nitroglycerin at which an enhanced flux rate is obtained using ethanol as a permeation enhancer. The system includes a membrane for controlling the rate at which nitroglycerin leaves the system. The patent defines a transdermal delivery device as a system controlled when $J_{net}/J_{system} \times 100 \geq 50\%$, where $J_{net}$ is the steady state in vitro drug input rate and $J_{system}$ is the in vitro steady state flux of the agent from the device directly into an infinite sink. This definition is based on the following relationship:

$$\frac{1}{J_{net}} = \frac{1}{J_{skin}} + \frac{1}{J_{system}}$$

where $J_{skin}$ is the in vivo or in vitro steady state flux of the agent directly through skin from a unit activity solution.

U.S. Pat. No. 4,593,048 discloses skin penetration enhancers comprising a lower alcohol containing 1–4 carbon atoms and at least one adjuvant. One of the adjuvant candidates consists of an aliphatic carboxylic acid monohydric alcohol ester containing 19–24 carbon atoms in total wherein the carboxylic acid moiety is a fatty acid moiety containing 18 carbon atoms and the alcohol moiety contains 1–6 carbon atoms.

U.S. Pat. No. 4,588,580 discloses a process for transdermal delivery of fentanyl and its derivatives using ethanol as a permeation enhancer.

U.S. Pat. No. 3,952,099 discloses compositions for skin permeation enhancement comprising a sugar ester in combination with a sulfoxide or phosphine oxide.

U.S. Pat. No. 3,896,238 discloses skin permeation enhancers comprising at least about 0.1 wt. % of a sugar ester and at least about 0.1 wt. % of a sulfoxide of the formula $R^1S(O)R^2$. The sugar ester is a member selected from the group consisting of sucrose monooctanoate, sucrose monodecanoate, sucrose monolaurate, sucrose monomyristate, sucrose monopalmitate, sucrose monostearate, sucrose monooleate and sucrose dioleate.

Hydromorphone and buprenorphine are known to have poor bioavailability due to extensive liver and intestinal metabolism. They can produce severe side effects, particularly respiratory depression on over dosage. It is therefore desirable to deliver these opioids non-orally and at a constant rate. Thus, it is an object of the present invention to provide transdermal delivery systems for drugs, particularly hydromorphone and buprenorphine, which can deliver the drug at therapeutically effective rates for extended periods of time. This objective is achieved by substantially enhancing the skin permeation of the drug and by adjusting the skin contact area of the transdermal delivery system.

Therefore, the present invention provides for transdermal delivery of drugs at therapeutically effective rates and offers the advantages of greatly increased drug permeability through the skin. Although it is known in the art to combine polar and non-polar components, the invention utilizes a novel combination of non-volatile components to achieve a combined synergistic effect which is a significant improvement and unexpectedly surprising in view of the use of either component, alone.

Other objects and advantages of the present invention will be apparent to those skilled in the art with reference to the attached drawings and the description of the invention which hereinafter follows.

SUMMARY OF THE INVENTION

The present invention comprises a composition of matter for application to a body surface or body membrane to deliver a drug at a therapeutically effective rate by permeation through the body surface or body membrane comprising, in combination, a dual permeation enhancer comprising sucrose cocoate and methyl laurate, and the drug to be delivered.

The present invention further provides a method for obtaining a therapeutically effective drug rate by permeation through a body surface or body membrane comprising, administering an effective amount of drug and simultaneously co-administering a dual permeation enhancer comprising sucrose cocoate and methyl laurate to the body surface or body membrane.

DESCRIPTION OF THE PREFERRED EMBODIMENTS

Figure 1:
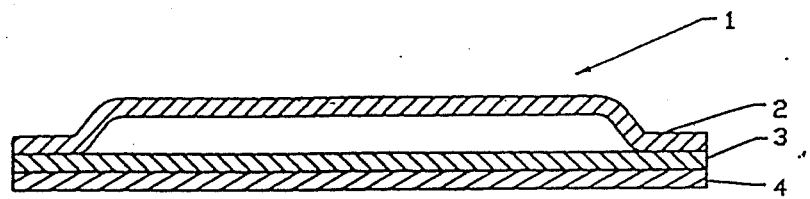
FIG. 1 is a cross-sectional view of a reservoir-type transdermal delivery system for administering a drug to a user through the skin.

In general, the scope of the invention encompasses a composition of matter comprising, in combination, a dual permeation enhancer comprising sucrose cocoate and methyl laurate, and a drug to be delivered to a body surface or body membrane. Specifically, the invention can be a unit dosage form and a method that co-administers a drug and a combination of two components, methyl laurate and sucrose cocoate, to a predetermined area of a user's unbroken skin for a predetermined time period.

In particular, the invention can be a unit dosage form for co-administering a drug, and a dual permeation enhancer comprising sucrose cocoate and methyl laurate, to a predetermined area of a user's unbroken skin for a predetermined time period comprising a membrane reservoir device comprising:
  (a) a backing layer that is substantially impermeable to the passage of drug, sucrose cocoate and methyl laurate, one face of which defines the uppermost exterior surface of said body;
  (b) a reservoir layer adjacent and below the opposite face that contains a supply of the drug, sucrose cocoate and methyl laurate;
  (c) a microporous membrane adjacent and below the reservoir layer through which the drug, and the dual permeation enhancer permeate;
  (d) a strippable layer, adjacent and below the microporous membrane, that is substantially impermeable to the drug and the dual permeation enhancer; and
  (e) means for attaching said unit dosage form to the user's skin.

The microporous membrane holds the drug and the dual permeation enhancer in the device. By removing the strippable layer, the device can be applied to the user's skin by the attaching means.

The invention can also be a unit dosage form for co-administering a drug, and a dual permeation enhancer comprising sucrose cocoate and methyl laurate, to a predetermined area of a user's unbroken skin for a predetermined time period comprising a laminate body comprising:
  (a) a backing layer that is substantially impermeable to the passage of drug, sucrose cocoate and methyl laurate, one face of which defines the uppermost exterior surface of said body;
  (b) a polymeric adhesive layer adjacent and below the opposite face that contains a supply of the drug, sucrose cocoate and methyl laurate; and
  (c) an impermeable strippable release liner adjacent and below the polymeric adhesive layer.

Furthermore, the invention can also be a method for co-administering a drug, and a dual permeation enhancer comprising sucrose cocoate and methyl laurate, to a predetermined area of a user's unbroken skin for a predetermined time period comprising:
  (a) administering the drug to the area continuously over the time period; and
  (b) simultaneously co-administering the dual permeation enhancer to the area of the skin at rates which are sufficient to substantially increase the permeability of the area of the skin to the drug.

The invention utilizes principles of transdermal drug delivery to provide a novel system for effectively administering drugs. The system is particularly useful in the transdermal delivery of hydromorphone and buprenorphine. Of particular significance is the use of a dual permeation enhancer comprising sucrose cocoate and methyl laurate, specifically to aid in the delivery of drugs across the skin. The combined effect of the components sucrose cocoate and methyl laurate as a dual permeation enhancer provides an unexpectedly surprising increase in the flux of drug across the skin, compared to the use of either component alone.

As used herein, the expression "drug" is intended to have its broadest interpretation as to any therapeutically active substance which is delivered through a living organism to produce a desired, usually beneficial, effect. The expression "drug" also includes all pharmaceutically acceptable salts thereof. In general, this includes therapeutic agents in all of the major therapeutic areas, including, but not limited to, anti-infectives such as antibiotics, antiviral agents, analgesics, analgesic combinations, anorexics, antiarthritics, antiasmatic agents, anticonvulsants, antidepressants, antidiabetic agents, antidiarraheals, antihistamines, antiinflammatory agents, antimigrain preparations, antimotion sickness preparations, antinauseants, antineoplastics, antiparkinsonism drugs, antipruritics, antipsychotics, antipyretics, antispasmodics including gastrointestinal and urinary, anticholinergics, sympathomimetrics, xanthine derivatives, cardiovascular preparations including calcium channel blockers, beta-blockers, antiarrythmics, antihypertensives, diuretics, vasodilators, including general, coronary, peripheral and cerebral, central nervous system stimulants, cough and cold preparations, decongestants, diagnostics, hormones, hypnotics, immunosuppressives, muscle relaxants, parasympatholytics, parasympathomimetrics, psychostimulants, sedatives, opioids and tranquilizers.

The term "opioid" means any natural or synthetic opioid analgesic such as morphine, oxymorphone, fentanyl, meperidine, propoxyphene, or oxycodone; any natural or synthetic narcotic antagonist such as nalmefene, naloxone or naltrexone; any natural or synthetic mixed opioid agonist/antagonist such as hydromorphone, nalbuphine, butrophanol, buprenorphine or pentazocine; or any pharmaceutically acceptable salt thereof.

The term "pharmaceutically acceptable salt" is intended to mean any non-toxic pharmaceutically acceptable salt of a drug which has therapeutic properties in mammals. Preparation of such salts is well known to those skilled in pharmaceuticals. By example, and not by way of limitation, pharmaceutically acceptable salts of opioids include acetates, napsylates, tosylates, succinates, hydrochlorides, palmitates, stearates, oleates, pamoates, laurates, valerates, hydrobromides, sulfates, methane sulfonates, tartrates, citrates, and maleates.

Specifically, the use of a dual permeation enhancer comprising sucrose cocoate and methyl laurate provides in vitro human cadaver skin flux rates for hydromorphone and buprenorphine which are therapeutically effective for at least 24 hours and for up to 72 hours. In vitro human cadaver skin permeation studies indicate that hydromorphone can be delivered at a rate within the range of 3-30 $\mu g/cm^2/hr.$, and preferably at a rate within the range of 10-20 $\mu g/cm^2/hr.$ for at least 24 hours and for up to 72 hours. In vitro human cadaver skin permeation studies also indicate that buprenorphine can be delivered at a rate within the range of about 1-10 $\mu g/cm^2/hr.$, and preferably at a rate within the range of 2-6 $\mu g/cm^2/hr$. By selecting a reasonable skin contact area for the inventive systems, therapeutic amounts of hydromorphone and buprenorphine can be delivered to a user's systemic circulation for analgesic purposes. Experiments have shown that a reasonable contact area is 5-90 $cm^2$ and preferably 10-40 $cm^2$. In addition, by optimizing the delivery system, hydromorphone and buprenorphine can be delivered at a constant rate over extended time periods without uncomfortable skin irritation.

Unit dosage forms which are capable of co-administering a drug and a permeation enhancer are well known in the transdermal art. Generally, these include skin-rate controlled devices and device-rate controlled devices.

Skin-rate control devices are those in which drug absorbtion is controlled by the rate of permeation through the skin. For example, U.S. Pat. Nos. 4,421,737; 4,310,509; and 3,428,043 disclose skin-rate controlled devices, all of which are incorporated herein by reference.

Device-rate controlled devices are those in which drug absorbtion is controlled by the rate of permeation of drug through a rate-controlling membrane. For example, U.S. Pat. Nos. 4,615,699; 3,948,262; 3,598,123; and 3,598,122 disclose device-rate controlled devices, all of which are incorporated herein by reference.

Referring now to FIG. 1, a preferred device 1 according to the present invention is disclosed. This device comprises a membrane reservoir system comprising an impermeable backing 2, a microporous membrane 3 and an impermeable strippable release liner 4. A gel composition is formulated with active drug and a dual permeation enhancer comprising sucrose cocoate and methyl laurate. Optionally, ethanol and/or other adjuvants may also be present in the gel composition. The resulting gel composition is loaded between the impermeable backing 2 and the microporous membrane 3. By removing the strippable release liner 4 prior to use, the device 1 can be applied to the skin by using an adhesive overlay or other attaching means.

The attaching means may be a contact adhesive layer adjacent and below the microporous membrane, one face of which defines a basal surface of the unit dosage form that contacts and adheres to the area of skin over the time period, and through which the drug, sucrose cocoate and methyl laurate permeate to the basal surface wherefrom they are absorbed by the area of the skin.

As used herein, the expression "adjuvant" means any pharmaceutically acceptable ingredient that improves the quality of the drug and the dual permeation enhancer. By way of example, and not by way of limitation, this includes stabilizers, gelling agents, preservatives, pH adjusters, water and inert fillers.

A reservoir gel formulation, applicable in the device of FIG. 1, which produces the required skin permeation rate for hydromorphone and buprenorphine is set forth in Table 1.

TABLE 1

| RESERVOIR GEL FORMULATION | |
|---|---|
| Component | w/w % |
| Drug (hydromorphone/buprenorphine) | 2-20 |
| Methyl laurate | 5-20 |
| Sucrose cocoate | 5-30 |
| Ethanol | 0-70 |
| Gelling agent | 2-10 |
| Inert filler or other additive | 0-10 |
| Water | balance |

Preferably, the reservoir gel layer comprises, on a weight percentage basis, from about 5 to about 15% drug, from about 5 to about 10% methyl laurate, from about 10 to about 35% sucrose cocoate, and from about 2 to about 5% of a gelling agent.

The gelling agent is added to the reservoir composition in order to form a viscous yet flowable drug and permeation enhancer gel mixture. The gelling agent allows the reservoir composition to exude through the membrane layer but prohibits the composition from simply pouring out upon removal of the strippable release liner.

The preferred gelling agent for the reservoir-type system is fumed silica. Hydroxypropyl cellulose, commercially available under the trade name Klucel ® GF from Hercules, Inc., is another applicable gelling agent. The optimum gel loading in the reservoir is in the range of 20-100 $mg/cm^2$ and preferably in the range of 30-80 $mg/cm^2$.

Preferable impermeable backing materials 2 include aluminized polyethylene, polypropylene, polyvinylchloride, and polyethylene terphthalate.

Preferable microporous reservoir membrane 3 materials include polypropylene and polyethylene.

Preferably, the impermeable release liner 4 should be coated with polypropylene or polyethylene so that it is heat-sealable and strippable from the reservoir membrane before application to a user's skin.

Figure 2:
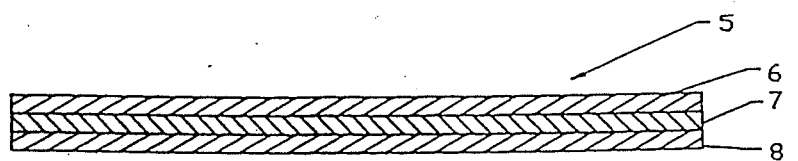
FIG. 2 is a cross-sectional view of a laminate matrix-type transdermal delivery system for administering a drug to a user through the skin.

Referring now to FIG. 2, another preferred embodiment of the present invention is disclosed. A skin-rate controlled laminate matrix-type transdermal delivery system 5 is shown comprising an impermeable backing layer 6, an impermeable strippable release liner 8 and a polymeric adhesive layer 7. The polymeric adhesive layer 7 contains a drug, sucrose cocoate and methyl laurate, in a suitable polymeric adhesive matrix material. The polymeric adhesive layer 7 is sandwiched between the impermeable backing layer 6 and the impermeable release liner 8. By removing the release liner 8, the device can be applied directly to the user's skin or by optionally using an adhesive overlay or other attaching means.

The polymeric adhesive layer 7 comprises a matrix which contains, on a weight percentage basis, from about 30 to about 70% of an adhesive polymer, from about 5 to about 20% of a drug, and from about 20 to about 45% of a dual permeation enhancer comprising a mixture of sucrose cocoate and methyl laurate. Optionally, from about 0.1 to about 5.5% of the polymeric adhesive layer may be comprised of conventional adjuvants, such as stabilizers and pH adjusters.

Preferably, the polymeric adhesive layer 7 comprises a matrix which contains, on a weight percentage basis, from about 50 to about 70% of an adhesive polymer, from about 5 to about 10% of a drug, and from about 20 to about 35% of a dual permeation enhancer comprising a mixture of sucrose cocoate and methyl laurate. Optionally, from about 0.1 to about 3% of the preferred polymeric adhesive layer may be comprised of conventional adjuvants, such as stabilizers and pH adjusters.

A typical polymeric adhesive layer formulation is set forth in Table 2.

TABLE 2

POLYMERIC ADHESIVE LAYER FORMULATION

| Component | w/w % |
|---|---|
| Drug | 5–20 |
| Sucrose cocoate | 10–35 |
| Methyl laurate | 5–20 |
| Other additives or adjuvants | 0–20 |
| Adhesive polymer | 30–70 |

The adhesive polymer should be a medically acceptable pressure sensitive adhesive, either water based or organic solvent based. Preferred adhesive polymers include polyacrylic polymers or vinyl acetate-acrylic multipolymers. A particularly preferred adhesive polymer is vinyl acetate-acrylic multipolymer solution available under the trade name Gelva® 788 through Monsanto Co.

A laminate matrix-type transdermal delivery system which produces the required skin permeation rate for hydromorphone HCl and buprenorphine HCl can be prepared as follows:

Hydromorphone HCl or buprenorphine HCl is dissolved in a mixture of sucrose cocoate and methyl laurate by adding potassium hydroxide and ethyl acetate. Sucrose cocoate is commercially available as a 48 wt. % aqueous solution. A stabilizer can also be added to the solution, if desired. The resulting solution is ultrasonicated for a few minutes, wherein an adhesive polymer is added to the solution and mixed for about 10 minutes to form an adhesive polymeric mixture. The mixture is then cast on an impermeable backing layer 6, such as an aluminized polyethylene film, to a thickness of about 0.1 to 2.0 mm. The cast adhesive mixture is then cured at about 50° C. to 80° C. for about 10 minutes. A release liner 8, such as a silicon or fluorocarbon coated release liner, is placed on the surface of the cured adhesive mixture. The laminate matrix-type system is then die-cut into an appropriate size and shape and placed into a hermetically sealed pouch.

The preferred transdermal delivery systems described above are further illustrated by the following nonlimiting examples:

EXAMPLE 1

A reservoir-type transdermal delivery system for buprenorphine HCl according to FIG. 1 was prepared as follows:

A solution containing 40 wt. % sucrose cocoate, 45 wt. % water, 10 wt. % methyl laurate and 4 wt. % fumed silica was prepared and stirred for about 3 hours to obtain a homogeneous gel. Thereafter, 3 wt. % buprenorphine HCl was dissolved in the gel by mixing and stirring for about 1 hour. About 60 mg/cm$^2$ of the resulting buprenorphine HCl gel was pouched between an impermeable backing 2 coated with polyethylene, and a microporous polyethylene membrane 3. Thereafter, the backing and membrane were joined about their peripheries by a heat seal. On top of the microporous polyethylene membrane 3, a polypropylene coated impermeable strippable release liner 4 was heat-sealed to the membrane.

The in vitro buprenorphine flux on human cadaver skin was measured at 35° C. using a standard Franz diffusion cell under sink conditions. A steady state buprenorphine flux of about 5 μg/cm$^2$/hr. was obtained within an hour. This flux stayed at a constant rate over 72 hours. During the 72 hour period, the reservoir-type system delivered 360 μg/cm$^2$ of buprenorphine HCl. Initially, the reservoir-type system contained about 1800 μg/cm$^2$ of buprenorphine HCl, indicating that about 20 wt. % of the loaded amount was transdermally delivered over the 72 hour period of time.

When the in vitro release rate of buprenorphine from the reservoir-type system was determined into an infinite sink, a rapid release of buprenorphine was observed through the microporous membrane and more than 70 wt. % of the loaded amount was depleted within the first 12 hours. Accordingly, the delivery mechanism of this system is not a device rate-controlled device as defined in U.S. Pat. No. 4,615,699.

EXAMPLE 2

A reservoir-type system similar to Example 1 was also prepared using hydromorphone HCl. The solution contained about 13 wt. % sucrose cocoate, about 13 wt. % water, about 17 wt. % methyl laurate and about 57 wt. % ethanol. Thereafter, about 4 wt. % hydroxypropyl cellulose (gelling agent - Klucel® GF) and about 6 wt. % hydromorphone HCl were added to the solution.

The hydromorphone HCl loading dose in the reservoir gel was about 2400 μg/cm$^2$. The pH of the reservoir gel was adjusted to about 6.5. The in vitro steady state skin permeation rate through human cadaver skin was determined to be about 16.7 μg/cm$^2$/hr. Thus, over a 3 day period of time, this corresponded to about a 50 wt. % delivery of the original loading dose.

EXAMPLE 3

A laminated matrix-type transdermal delivery system for buprenorphine HCl was prepared according to FIG. 2. 5.5 wt. % buprenorphine HCl was dissolved in a mixture containing 7.5 wt. % ethyl acetate, 20 wt. % sucrose cocoate aqueous solution, 5 wt. % methyl laurate, and 0.5 wt. % potassium hydroxide. Thereafter, 61.5 wt. % of an adhesive vinyl acetate-acrylate multipolymer solution (Gelva® 788, Monsanto Co.) was added to the solution and mixed until the final mixture became homogeneous. The resulting homogeneous mixture was cast onto an impermeable layer 6 approximately 0.5 mm thick and the layer was cured for 10 minutes at 70° C. After curing, the adhesive layer was covered with an impermeable strippable release liner 8.

The in vitro buprenorphine flux through human cadaver skin was measured according to the procedure described in Example 1. The steady state buprenorphine flux was about 3.5 μg/cm$^2$/hr. which was obtained in about 7 to 9 hours after application. The steady state flux remained substantially constant over a 72 hour period of time.

EXAMPLE 4

The unexpected permeation enhancement effect due to the combination of sucrose cocoate and methyl laurate is shown as follows:

For the evaluation of the degree of permeation enhancement, saturated test solutions of buprenorphine HCl in methyl laurate and/or sucrose cocoate were directly applied onto the epidermis side of human cadaver skin loaded between donor and receptor compartments of a standard Franz diffusion cell. The cell was kept at 35° C. during the diffusion study. The in vitro flux of buprenorphine through human cadaver skin into an infinite sink are listed in Table 3 for the standard test solutions. The sucrose cocoate used for the test is commercially available in a 48 wt. % aqueous solution under the trade name Crodesta ® SL-40, through Croda, Inc.

TABLE 3

| SKIN FLUX OF BUPRENORPHINE HCl ($\mu g/cm^2/day$) | |
|---|---|
| Solution A | 8 |
| Solution B | 100 |
| Solution A:B(1:9) | 226 |

Solution A:100 wt. % methyl laurate
Solution B:48 wt. % sucrose cocoate aqueous solution Table 3 indicates that the addition of 10 wt. % methyl laurate to an aqueous solution of sucrose cocoate shows substantial penetration enhancement effects as compared to 100 wt. % methyl laurate or sucrose cocoate aqueous solutions alone.

EXAMPLE 5

A series of tests similar to Example 4 were conducted utilizing solutions saturated with different drugs and the results are listed in Table 4.

TABLE 4

| PERMEATION ENHANCEMENT BY THE COMBINATION OF METHYL LAURATE AND SUCROSE COCOATE | | | |
|---|---|---|---|
| | Flux ($\mu g/cm^2/day$) | | |
| Drugs | Solution A | Solution B | Solution A:B(3:7) |
| Dichlofenac Sodium | 14 | 146 | 215 |
| Prednisolone | 51 | 8 | 188 |
| Nifedipine | 15 | 14 | 23 |
| Ibuprofen | 586 | 547 | 1897 |
| Estradiol | 4.3 | 7.4 | 19.9 |

Solution A:100 wt. % methyl laurate
Solution B:48 wt. % sucrose cocoate aqueous solution The combination of 30 wt. % methyl laurate with an aqueous solution of sucrose cocoate shows substantial penetration enhancement effects on different drugs as compared to the use of 100 wt. % methyl laurate or sucrose cocoate aqueous solution alone.

The present invention may be embodied in other specific forms without departing from the spirit or essential attributes thereof and, accordingly, reference should be made to the appended claims, rather than to the foregoing specification, as indicating the scope of the invention.

I claim:

1. A unit dosage form for co-administering a drug, and a dual permeation enhancer comprising sucrose cocoate and methyl laurate, to a predetermined area of a user's unbroken skin for a predetermined time period comprising a membrane reservoir device comprising:
   (a) a backing layer that is substantially impermeable to the passage of drug, sucrose cocoate and methyl laurate, one face of which defines the uppermost exterior surface of said body;
   (b) a reservoir layer adjacent and below the opposite face that contains a supply of the drug, sucrose cocoate and methyl laurate said sucrose cocoate being present in an amount from about 5% to 35% on a weight percentage basis and said methyl laurate being present in an amount from about 5% to 20% on a weight percentage basis;
   (c) a microporous membrane adjacent and below the reservoir layer through which the drug and the dual permeation enhancer permeate;
   (d) a strippable layer, adjacent and below the microporous membrane, that is substantially impermeable to the drug and the dual permeation enhancer; and
   (e) means for attaching said unit dosage form to the user's skin.

2. The unit dosage form of claim 1 wherein the attaching means is a contact adhesive layer adjacent and below the microporous membrane, one face of which defines a basal surface of the unit dosage form that contacts and adheres to the area of skin over the time period, and through which the drug, sucrose cocoate and methyl laurate permeate to the basal surface wherefrom they are absorbed by the area of the skin.

3. The unit dosage form of claim 1 wherein the reservoir layer comprises, on a weight percentage basis, from about 2 to about 20% drug, from about 5 to about 20% methyl laurate, from about 5 to about 30% sucrose cocoate and from about 2 to about 10% of a gelling agent.

4. The unit dosage form of claim 1 wherein the reservoir layer comprises, on a weight percentage basis, from about 5 to about 15% drug, from about 5 to about 10% methyl laurate, from about 10 to about 35% sucrose cocoate, and from about 2 to about 5% of a gelling agent.

5. The unit dosage form of claim 3 wherein the gelling agent is selected from the group consisting of fumed silica and hydroxypropyl cellulose.

6. The unit dosage form of claim 1 wherein said drug is selected from the group consisting of hydromorphone, buprenorphine, dichlofenac sodium, prednisolone, nifedipine, ibuprofen and estradiol.

7. A unit dosage form for co-administering a drug, and a dual permeation enhancer comprising sucrose cocoate and methyl laurate, to a predetermined area of a user's unbroken skin for a predetermined time period comprising a laminate body comprising:
   (a) a backing layer that is substantially impermeable to the passage of drug, sucrose cocoate and methyl laurate, one face of which defines the uppermost exterior surface of said body;
   (b) a polymeric adhesive layer adjacent and below the opposite face that contains a supply of the drug, sucrose cocoate and methyl laurate said sucrose cocoate being present in an amount from about 5% to 35% on a weight percentage basis and said methyl laurate being present in an amount from about 5% and 20% on a weight percentage basis; and
   (c) an impermeable strippable release liner adjacent and below the polymeric adhesive layer.

8. The unit dosage form of claim 7 wherein the polymeric adhesive layer comprises a drug, sucrose cocoate, methyl laurate, and a suitable adhesive polymer.

9. The unit dosage form of claim 8 wherein the polymeric adhesive layer further comprises at least one adjuvant.

10. The unit dosage form of claim 7 wherein the polymeric adhesive layer comprises a matrix which contains, on a weight percentage basis, from about 30 to about 70% of an adhesive polymer, from about 5 to about 20% of a drug, and from about 20 to about 45% of a dual permeation enhancer comprising a mixture of sucrose cocoate and methyl laurate.

11. The unit dosage form of claim 7 wherein the polymeric adhesive layer comprises a matrix which contains, on a weight percentage basis, from about 50 to about 70% of an adhesive polymer, from about 5 to about 10% drug, from about 20 to about 35% of a dual permeation enhancer comprising a mixture of sucrose cocoate and methyl laurate.

12. The unit dosage form of claim 8 wherein said suitable adhesive polymer is selected from the group consisting of a polyacrylic polymer and a vinyl acetate-acrylate multipolymer.

13. The unit dosage form of claim 7 wherein said drug is selected from the group consisting of buprenorphine, dichlofenac sodium, prednisolone, nifedipine, ibuprofen and estradiol.

* * * * *